United States Patent [19]

Takahashi et al.

[11] Patent Number: 5,252,580
[45] Date of Patent: Oct. 12, 1993

[54] INDOLE DERIVATIVES AND ANTI-ULCER COMPOSITIONS THEREOF

[75] Inventors: Toshihiro Takahashi; Hitoshi Inoue, both of Saitama; Masato Horigome, Tokyo; Kenichi Momose, Saitama; Masanori Sugita, Saitama; Kouichi Katsuyama, Saitama; Chikako Suzuki, Saitama; Shinji Nagai, Saitama; Masao Nagase, Saitama; Koichi Nakamaru, Saitama, all of Japan

[73] Assignee: Nisshin Flour Milling Co., Ltd., Tokyo, Japan

[21] Appl. No.: 947,169

[22] Filed: Sep. 18, 1992

[30] Foreign Application Priority Data

Sep. 30, 1991 [JP] Japan .................. 3-276333

[51] Int. Cl.$^5$ .................. A61K 31/445; C07D 401/06
[52] U.S. Cl. ..................... 514/292; 514/183; 514/217; 514/285; 540/471; 540/555; 540/557; 546/64; 546/86; 546/87
[58] Field of Search ............. 546/87, 86, 64; 514/183, 217, 285, 292; 540/471, 555, 557

[56] References Cited

U.S. PATENT DOCUMENTS

| | | | |
|---|---|---|---|
| 2,852,520 | 9/1958 | Robinson | 260/295 |
| 4,005,206 | 1/1977 | Gaignault et al. | 546/87 X |
| 4,933,345 | 6/1990 | Huth et al. | 546/86 X |

OTHER PUBLICATIONS

D. A. Shirley et al. JACS 75 (1953) 375-378.
A. J. Elliot et al. Tetrahedron Lett. 23, 1983-84 (1982).
A. M. Welch et al. J. Med. Chem. 29 2093-99 (1986).
G. Schill et al. Tetrahedron 43 (1987) 3729-45.
P. Magnus et al. JCS, Chem. Commun. (1989) 518-520.
Sakai et al. Yakugaku Zasshi 97 (3) 309-319 (1977).
B. E. Maryanoff et al. JOC, 43 2733 (1978).
Sakai et al. Chem. Pharm. Bull. 28, 2527-2530 (1980).
Sakai et al., Chem. abst. vol. 116, 214762n (1992).

Primary Examiner—Joseph Paul Brust
Assistant Examiner—Jacqueline Haley
Attorney, Agent, or Firm—Abelman Frayne & Schwab

[57] ABSTRACT

Disclosed are indole derivatives of formula (I)

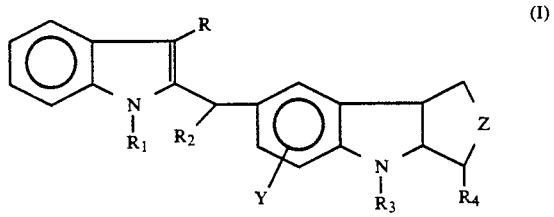

wherein
Y represents H, $C_1$-$C_6$ alkyl, $C_1$-$C_6$ alkoxy or halogen;
Z represents —$CH_2N(R_5)$—;
R represents H or —$CH_2CH_2X$ where X represents pyridyl, aralkyloxy or substituted amino of $NR_6R_7$ where $R_6$ represents H, $C_1$-$C_6$ alkyl, aralkyl, $C_1$-$C_6$ alkoxycarbonyl, aralkyloxycarbonyl or halogenated $C_1$-$C_6$ alkoxycarbonyl and $R_7$ represents H, $C_1$-$C_6$ alkyl or aralkyl, or together with $R_2$ may form a ring of —$(CH_2)_n$— (n is 1-4) or

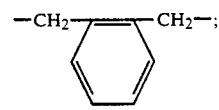

$R_1$ represents H, $C_1$-$C_6$ alkyl, aralkyl or arylsulfonyl;
$R_2$ represents $C_1$-$C_6$ alkyl, hydroxy, $C_1$-$C_6$ alkoxy or aralkyloxy;
$R_3$ represents H, $C_1$-$C_6$ alkyl, aralkyl or halogenated $C_1$-$C_6$ alkyl;
$R_4$ and $R_5$ may be the same or different and each represents H, $C_1$-$C_6$ alkyl or aralkyl or both may together form a ring of —$(CH_2)_m$— (m is 3 or 4);
or pharmaceutically acceptable acid addition salts thereof. They are useful as an antiulcer agent.

10 Claims, No Drawings

INDOLE DERIVATIVES AND ANTI-ULCER COMPOSITIONS THEREOF

FIELD OF THE INVENTION

This invention relates to new indole derivatives and pharmaceutical compositions comprising them which are useful as antiulcer agents.

BACKGROUND OF THE INVENTION

Known medicaments which have been used as antiulcer agents include $H_2$-receptor antagonists representative of which is cimetidine, gastric acid secretion inhibitors such as omeprazole inhibiting proton pump ($H^+$, $K^+$-ATPase) and medicaments having gastric mucosa protection activity, which are chosen depending on the symptom of patients. However those medicaments are of such disadvantages as generally weak activity and occurrence of side effects. For instance, cimetidine, representative of $H_2$-receptor antagonists have encountered the presence of intractable ulcer. Omeprazole has sufferred from the occurrence of carcinoid and the interaction with other drugs including diazepam and phenytoin such as a lowering of hepatic clearance. Thus there is a continuing need for effective antiulcer agents.

The present invention results from efforts to develop new indole derivatives with more improved antiulcer effect.

DISCLOSURE OF THE INVENTION

According to the invention, there are provided indole derivatives of formula (I)

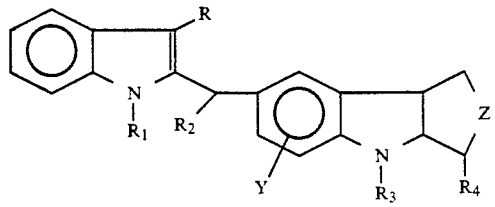

wherein

Y represents H, $C_1$-$C_6$ alkyl, $C_1$-$C_6$ alkoxy or halogen;

Z represents —$CH_2N(R_5)$—;

R represents H or —$CH_2CH_2X$ where X represents pyridyl, aralkyloxy or substituted amino of $NR_6R_7$ where $R_6$ represents H, $C_1$-$C_6$ alkyl, aralkyl, $C_1$-$C_6$ alkoxycarbonyl, aralkyloxycarbonyl or halogenated $C_1$-$C_6$ alkoxycarbonyl and $R_7$ represents H, $C_1$-$C_6$ alkyl or aralkyl, or together with $R_2$ may form a ring of —$(CH_2)_n$— (n is 1-4) or

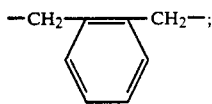

$R_1$ represents H, $C_1$-$C_6$ alkyl, aralkyl or arylsulfonyl;
$R_2$ represents $C_1$-$C_6$ alkyl, hydroxy, $C_1$-$C_6$ alkoxy or aralkyloxy;
$R_3$ represents H, $C_1$-$C_6$ alkyl, aralkyl or halogenated $C_1$-$C_6$ alkyl;

$R_4$ and $R_5$ may be the same or different and each represents H, $C_1$-$C_6$ alkyl or aralkyl or both may together form a ring of —$(CH_2)_m$— (m is 3 or 4);

or pharmaceutically acceptable acid addition salts thereof.

Suitable pharmaceutically acceptable acid addition salts of the compounds of formula (I) include acid addition salts formed with organic or inorganic acids such as hydrochlorides, hydrobromides, sulfates, phosphates, acetates, succinates, citrates, tartrates, fumarates and maleates.

There can be cis, trans isomers at the pyrido[3,4-b]indole or pyrido[4,3-b]indole moiety in the compounds of formula (I). Those isomers are also included within the scope of the present invention.

In the definition of formula (I), $C_1$-$C_6$ alkyl represented by Y, $R_6$, $R_7$, $R_1$, $R_2$, $R_3$, $R_4$ and $R_5$ includes, for example, methyl, ethyl, n-propyl, isopropyl, n-butyl, isobutyl and n-hexyl. $C_1$-$C_6$ alkoxy represented by Y and $R_2$ and the $C_1$-$C_6$ alkoxy portion in $R_6$ include, for example, methoxy, ethoxy, n-propoxy, isopropoxy, n-butoxy, isobutoxy and n-hexyloxy. Aralkyl represented by $R_6$, $R_7$, $R_1$, $R_3$, $R_4$ and $R_5$ includes e.g., benzyl and phenethyl and aralkyloxy represented by X and $R_2$ includes e.g., benzyloxy and phenethyloxy. $C_1$-$C_6$ alkoxycarbonyl represented by $R_6$ includes e.g., methoxycarbonyl, ethoxycarbonyl, n-propoxycarbonyl, isopropoxycarbonyl, n-butoxycarbonyl, isobutoxycarbonyl and n-hexyloxycarbonyl. Aralkyloxycarbonyl represented by $R_6$ includes e.g., $COOCH_2Ph$ and $COOCH_2CH_2Ph$. Halogenated $C_1$-$C_6$ alkyl represented by $R_3$ includes e.g., —$CH_2CF_3$, —$CH_2CH_2CF_3$, and halogenated $C_1$-$C_6$ alkoxycarbonyl represented by $R_6$ includes e.g., —$COOCH_2CCl_3$, —$COOCH_2CH_2CCl_3$. Arylsulfonyl includes e.g., p-toluenesulfonyl(tosyl). When $R_7$ and $R_2$ form together a ring, —$(CH_2)_n$— may be, for example, —$(CH_2)_3$— and —$(CH_2)_4$—. When $R_4$ and $R_5$ form together a ring, —$(CH_2)_m$— may be, for example, —$(CH_2)_4$—. Halogen includes e.g., fluorine, chlorine and bromine. The subsequent Y may be at any position in the benzene ring.

Representative compounds of formula (I) are listed below.

4a,9a-cis-6-(3-Benzyloxycarbonyl-1,2,3,4,5,6,7,8-octahydroazecino[5,4-b]indole-8-yl)-2,9-dimethyl-1,2,3,4,4a, 9a-hexahydro-pyrido[3,4-b]indole, 6-(3-Ethoxycarbonyl-1,2,3,4,5,6,7,8-octahydroazecino[5,4-b]indole-8-yl)-2-ethyl-9-methyl-1,2,3,4,4a,9a-hexahydropyrido[3,4-b]indole, 6-(3-Benzyloxycarbonyl-1,2,3,4,5,6,7,8-octahydroazecino[5,4-b]indole-8-yl)-2,9-diethyl-1,2,3,4,4a,9a-hexahydropyrido[3,4-b]indole, 6-(3-Ethoxycarbonyl-1,2,3,4,5,6,7,8-octahydroazecino[5,4-b]indole-8-yl)-2,9-diethyl-1,2,3,4,4a,9a-hexahydropyrido[3,4-b]indole, 6-(3-Ethoxycarbonyl-1,2,3,4,5,6,7,8-octahydroazecino[5,4-b]indole-8-yl)-2-ethyl-9-(2,2,2-trifluoroethyl)-1,2,3,4,4a,9a-hexahydro-pyrido[3,4-b]indole, 2-Benzyl-6-(3-ethoxycarbonyl-1,2,3,4,5,6,7,8-octahydroazecino[5,4-b]indole-8-yl)-9-methyl-1,2,3,4,4a,9a-hexahydropyrido[3,4-b]indole, 9-(3-Ethoxycarbonyl-1,2,3,4,5,6,7,8-octahydroazecino[5,4-b]indole-8-yl)-12-methyl-1,2,3,4,7,12b-hexahydro-4H-indolo[2,3-a]quinolizine, 2,9-Diethyl-6-(3-(2,2,2-trichloroethoxycarbonyl)-1,2,3,4,5,6,7,8-octahydro-azecino[5,4-b]indole-8-yl)-1,2,3,4,4a,9a-hexahydro-pyrido[3,4-b]indole, 6-(13-Ethoxycarbonyl-6,7,12,13,14,15-hexahydrobenzo[h]azecino[5,4-b]indole-6-yl)-2,9-diethyl-1,2,3,4,4a,9a-hexahydro-pyrido[3,4-b]indole, 6-(13-Benzyloxycarbonyl-6,7,12,13,14,15-hexahydrobenzo[h]azecino[5,4-b]indole-6-yl)-2,9-diethyl-1,2,3,4,4a,9a-hexahydro-pyrido[3,4-b]indole, 6-(3-Benzyloxycarbonyl-1,2,4,5,6,7-hexahydro-3H-azonino[5,4-b]indole-7-yl)-2,9-diethyl-1,2,3,4,4a,9a-hexahydropyrido[3,4-b]indole, 4a,9a-trans-6-(3-Benzyloxycarbonyl-1,2,4,5,6,7-hexahydro-3H-azonino[5,4-b]indole-7-yl)-2,9-dimethyl-1,2,3,4,4a,9a-hexahydro-pyrido[3,4-b]indole, 4a,9a-trans-6-(3-Benzyloxycarbonyl-1,2,4,5,6,7-hexahydro-3H-azonino[5,4-b]indole-7-yl)-1,2,9-trimethyl-1,2,3,4,4a,9a-hexahydro-pyrido[3,4-b]indole, 4a,9a-trans-6-(3-Benzyloxycarbonyl-1,2,4,5,6,7-hexahydro-3H-azonino[5,4-b]indole-7-yl)-1-ethyl-2,9-dimethyl-1,2,3,4,4a,9a-hexahydro-pyrido[3,4-b]indole, 4a,9a-trans-1,9a-trans-6-(3-Ethoxycarbonyl-1,2,4,5,6,7-hexahydro-3H-azonino[5,4-b]indole-7-yl)-2,9-diethyl-1-phenethyl-1,2,3,4,4a,9a-hexahydro-pyrido[3,4-b]indole, 4a,9a-cis-1,9a-trans-6-(3-Ethoxycarbonyl-1,2,4,5,6,7-hexahydro-3H-azonino[5,4-b]indole-7-yl)-2,9-diethyl-1-phenethyl-1,2,3,4,4a,9a-hexahydro-pyrido[3,4-b]indole, 1,9a-trans-4a,9a-trans-6-(3-Ethoxycarbonyl-1,2,4,5,6,7-hexahydro-3H-azonino[5,4-b]indole-7-yl)-2-ethyl-1-phenethyl-1,2,3,4,4a,9a-hexahydro-pyrido[3,4-b]indole, 6-(1-(3-(2-Benzyl(ethoxycarbonyl)aminoethyl)-indole-2-yl)ethyl)-2,9-diethyl-1,2,3,4,4a,9a-hexahydro-pyrido[3,4-b]indole, 6-(1-(3-(2-Benzyl(benzyloxycarbonyl)aminoethyl)-indole-2-yl)ethyl)-2,9-diethyl-1,2,3,4,4a,9a-hexahydro-pyrido[3,4-b]indole, 6-(1-(3-(2-Ethyl(benzyloxycarbonyl)aminoethyl)-indole-2-yl)ethyl)-2,9-diethyl-1,2,3,4,4a,9a-hexahydro-pyrido[3,4-b]indole, 6-(1-(3-(2-Ethyl(ethoxycarbonyl)aminoethyl)-indole-2-yl)ethyl)-2,9-diethyl-1,2,3,4,4a,9a-hexahydro-pyrido[3,4-b]indole, 2,9-Diethyl-6-(3-(2-dibenzylaminoethyl)-1-tosyl-indole-2-yl)hydroxymethyl-1,2,3,4,4a,9a-hexahydro-pyrido[3,4-b]indole, 2,9-Diethyl-6-(3-(2-dibenzylaminoethyl)-1-methyl-indole-2-yl)hydroxymethyl-1,2,3,4,4a,9a-hexahydro-pyrido[3,4-b]indole, 2,9-Diethyl-6-(3-(2-dibenzylaminoethyl)-1-benzyl-indole-2-yl)hydroxymethyl-1,2,3,4,4a,9a-hexahydro-pyrido[3,4-b]indole, 2,9-Diethyl-6-(1-methyl-indole-2-yl)hydroxymethyl-1,2,3,4,4a,9a-hexahydro-pyrido[3,4-b]indole, 2,9-Diethyl-6-(3-(2-benzyloxyethyl)-1-methyl-indole-2-yl)hydroxymethyl-1,2,3,4,4a,9a-hexahydro-pyrido[3,4-b]indole, 2,9-Diethyl-6-(3-(2-pyridyl)ethyl)-1-tosyl-indole-2-yl)hydroxymethyl-1,2,3,4,4a,9a-hexahydro-pyrido[3,4-b]indole, 2,9-Diethyl-6-(3-(2-benzyloxyethyl)-1-benzyl-indole-2-yl)hydroxymethyl-1,2,3,4,4a,9a-hexahydro-pyrido[3,4-b]indole, 2,9-Diethyl-6-(1-(3-(2-methylethylamino)ethyl)-indole-2-yl)ethyl-1,2,3,4,4a,9a-hexahydro-pyrido[3,4-b]indole, 2-Ethyl-6-(3-methyl-1,2,3,4,5,6,7,8-octahydro-azecino[5,4-b]indole-8-yl)-9-methyl-1,2,3,4,4a,9a-hexahydro-pyrido[3,4-b]indole, 2,9-Diethyl-6-(13-methyl-6,7,12,13,14,15-hexahydrobenzo[h]azecino[5,4-b]indole-6-yl)-1,2,3,4,4a,9a-hexahydropyrido[3,4-b]indole, 9-(3-Methyl-1,2,3,4,5,6,7,8-octahydro-azecino[5,4-b]indole-8-yl)-12-methyl-1,2,3,4,5,12b-hexahydro-4H-indolo[2,3-a]quinolizine, 8-(3-Benzyloxycarbonyl-1,2,4,5,6,7-hexahydro-3H-azonino[5,4-b]indole-7-yl)-5-ethyl-2,6-dimethyl-1,2,3,4,4a,9b-hexahydropyrido[4,3-b]indole, 8-(3-Benzyloxycarbonyl-1,2,4,5,6,7-hexahydro-3H-azonino[5,4-b]indole-7-yl)-6-chloro-5-ethyl-2-methyl-1,2,3,4,4a,9b-hexahydro-pyrido[4,3-b]indole, 8-(3-Benzyloxycarbonyl-1,2,4,5,6,7-hexahydro-3H-azonino[5,4-b]indole-7-yl)-2,5-dimethyl-6-methoxy-1,2,3,4,4a,9b-hexahydro-pyrido[4,3-b]indole 4a,9b-cis-8-(3-Benzyloxycarbonyl-1,2,4,5,6,7-hexahydro-3H-azonino[5,4-b]indole-7-yl)-5-ethyl-2-methyl-1,2,3,4,4a,9b-hexahydro-pyrido[4,3-b]indole, 4a,9b-trans-8-(3-Benzyloxycarbonyl-1,2,4,5,6,7-hexahydro-3H-azonino[5,4-b]indole-7-yl)-5-ethyl-2-methyl-1,2,3,4,4a,9b-hexahydro-pyrido[4,3-b]indole, 4a,9b-cis-8-(3-Benzyloxycarbonyl-1,2,4,5,6,7-hexahydro-3H-azonino[5,4-b]indole-7-yl)-5-benzyl-2-methyl-1,2,3,4,4a,9b-hexahydro-pyrido[4,3-b]indole, 4a,9b-cis-8-(3-Benzyloxycarbonyl-1,2,4,5,6,7-hexahydro-3H-azonino[5,4-b]indole-7-yl)-2,5-dimethyl-1,2,3,4,4a,9b-hexahydro-pyrido[4,3-b]indole, 4a,9b-trans-8-(3-Benzyloxycarbonyl-1,2,4,5,6,7-hexahydro-3H-azonino[5,4-b]indole-7-yl)-2,5-dimethyl-1,2,3,4,4a,9b-hexahydro-pyrido[4,3-b]indole, 4a,9b-cis-8-(3-Benzyloxycarbonyl-1,2,4,5,6,7-hexahydro-3H-azonino[5,4-b]indole-7-yl)-2,5-diethyl-1,2,3,4,4a,9b-hexahydro-pyrido[4,3-b]indole, 4a,9b-trans-8-(3-Benzyloxycarbonyl-1,2,4,5,6,7-hexahydro-3H-azonino[5,4-b]indole-7-yl)-2,5-diethyl-1,2,3,4,4a,9b-hexahydro-pyrido[4,3-b]indole, 4a,9b-cis-8-(3-Benzyloxycarbonyl-1,2,4,5,6,7-hexahydro-3H-azonino[5,4-b]indole-7-yl)-2-benzyl-5-ethyl-1,2,3,4,4a,9b-hexahydro-pyrido[4,3-b]indole, 4a,9b-trans-8-(3-Benzyloxycarbonyl-1,2,4,5,6,7-hexahydro-3H-azonino[5,4-b]indole-7-yl)-2-benzyl-5-ethyl-1,2,3,4,4a,9b-hexahydro-pyrido[4,3-b]indole.

The compounds of formula (I) can be prepared by condensing the compound of formula (II) with the compound of formula (IV) or the compound of formula (III) with the compound of formula (V) in accordance with known methods, for instance G. Schill et al. method mentioned in Tetrahedron 43 (1987) 3729, ibid 43 (1987) 3747; P. Magnus et al. method mentioned in JCS Chem. Commun. (1989) 518; Sakai et al. method mentioned in Yakugaku Zasshi 97 (3) 309; and D. A. Shirley et al. method mentioned in JACS 75 (1953) 375. Preferred embodiment is shown by the following reactions (1) and (2).

Reaction (1)

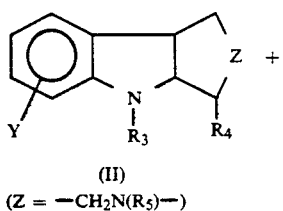

(II)
(Z = —CH$_2$N(R$_5$)—)

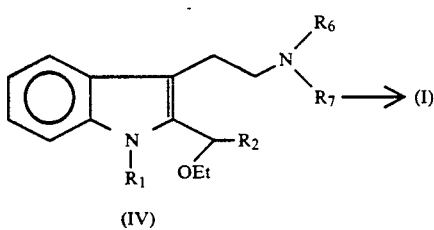

Reaction (2)

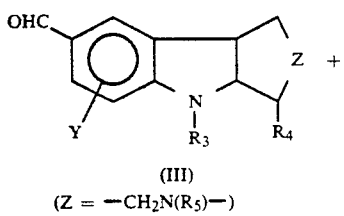

(III)
(Z = —CH$_2$N(R$_5$)—)

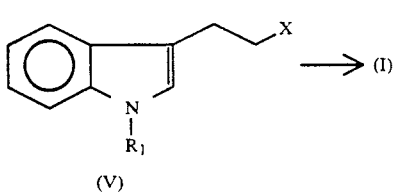

(V)

In reaction (1), the compounds of formulas (II) and (IV) are reacted in the presence of an acid catalyst using an alcoholic solvent such as methanol and ethanol. Preferred acids are inorganic acids such as hydrochloric acid. The reaction is usually carried out at a temperature between room temperature and a boiling point of the solvent used.

In reaction (2), the compound of formula (V) is converted with butyl lithium or the like to the 2-lithioindole derivative which is then reacted with the compound of formula (III). The reaction is preferably carried out at a temperature in the range of −70° C. to room temperature using an inert solvent such as tetrahydrofuran and ether.

If R$_6$ is formate in the compounds of formula (I) prepared in reactions (1) and (2), R$_6$ can be converted to alkyl by reduction of the formate with a reducing agent such as lithium aluminum hydride. If R$_2$ is hydroxy, R$_2$ can be converted to alkoxy or aralkyloxy by a conventional alkylation process.

The compounds of formulas (II) and (III) used in the invention can be prepared by a variety of methods. As shown in the following reaction scheme, those methods include the process of alkylating tetrahydro-β-carboline or tetrahydro-γ-carboline derivatives of formula (VI), reducing the indole nucleus to the compound of formula (IX) and alkylating it to the compound of formula (II); the process of dialkylating the compound of formula (VI) to the compound of formula (VIII) followed by reduction of the indole nucleus; and the process of reductively alkylating the compound of formula (VII) to the compound of formula (II). The reduction or reductive alkylation of the indole nucleus employed in the invention is carried out according to A. J. Elliot et al. method described in Tetrahedron Lett. 23, 1983 (1982), W. M. Welch et al. method described in J. Med. Chem. 29, 2093 (1986) or B. E. Maryanoff et al. method described in JOC, 43, 2733 (1978). In an alkylation of the compounds of formulas (VI) and (IX), some known methods may be applied, for example the reaction with halogenated alkyl or aralkyl such as alkyliodide or benzyl chloride using a variety of bases such as sodium carbonate, diisopropylamine, sodium hydride or the like in an inert solvent such as dimethylformamide, dimethylsulfoxide, tetrahydrofuran, ethanol, methanol or the like. The compounds of formula (III) can be prepared by formylating the compounds of formula (II) as prepared above by Vilsmeier's method.

Further, the compounds of formula (IV) wherein R$_2$ and R$_7$ form together a ring can be synthesized, for example, by ring opening reaction of the indoloquinolizine or indoloindoline derivatives according to Sakai et al. method described in Chem. Pharm. Bull. 28, 2527 (1980). The compounds of formula (V) can be synthesized by known alkylation, arylsulfonylation or the like from the starting material such as tryptamine, tryptophol or the like.

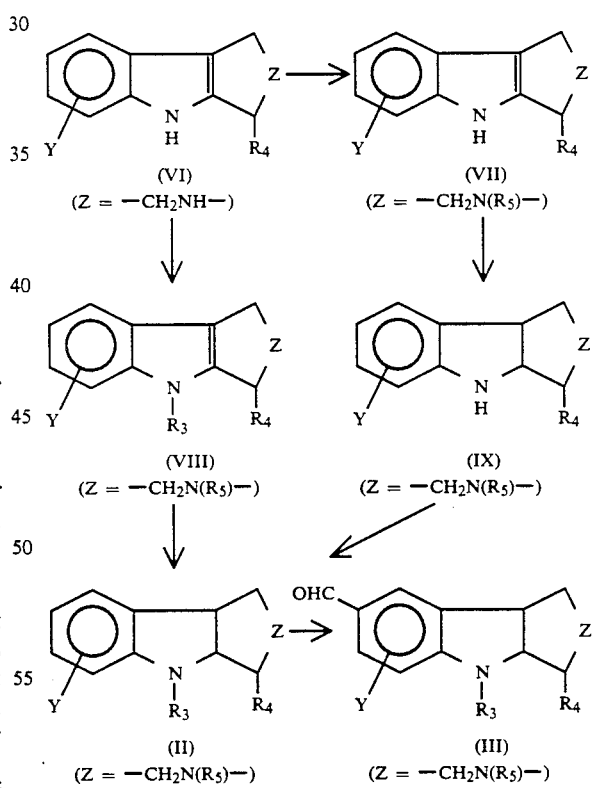

The compounds of formula (I) and their pharmaceutically acceptable salts exert an anti-secretory effect by inhibition of H$^+$/K$^+$ATPase.

Thus the invention also provides a pharmaceutical composition which comprises as an active ingredient an effective amount of the compounds of formula (I) or pharmaceutically acceptable acid addition salts thereof. Such composition may be formulated in conventional manner using one or more pharmaceutically acceptable carriers and/or excipients.

The compounds of formula (I) and their pharmaceutically acceptable salts inhibit exogenously and endogenously stimulated gastric acid secretion and are useful as an antiulcer agent in the treatment of gastrointestinal diseases such as gastric and duodenal ulcers, gastritis, reflux esophagitis and Zollinger-Ellison Syndrome.

The compounds of the invention can usually be administered orally or parenterally in the form of various pharmaceutical preparations. For oral administration, the pharmaceutical compositions may take the form of solid preparations including tablets such as sugar-coated tablets, capsules such soft and hard capsules and liquid preparations such as solutions, emulsions or suspensions. For parenteral administration, the compositions may take the form of injections. Such solid preparations can be prepared by conventional means with pharmaceutically acceptable excipients such as binding agents, fillers, lubricants, disintegrants or wetting agents. Such liquid preparations can be prepared by conventional means with pharmaceutically acceptable additives such as suspending agents, emulsifying agents, non-aqueous vehicles and preservatives. The preparations may also contain buffer salts, flavoring, coloring and sweetening agents if desired.

The active ingredient is contained in the formulation in an amount of 0.1–100% by weight, suitably 1–50% by weight in the case of formulations for oral administration and 0.2–20% by weight in the case of formulations for injection based on the weight of the formulation.

Route and dosage of administration for the compounds of the invention are not specifically limited and are appropriately chosen depending upon form of the formulation, age and sex of the patient, severity of the disease and other factors. Daily dosage of the active ingredient is 1 mg to 2000 mg.

The invention is further illustrated by the following non-limitative examples, before which the referential examples are given for illustrating the synthesis of the starting materials used in the preparation of the present compounds.

REFERENTIAL EXAMPLE 1

Synthesis of Compound (II)

(1)

4a,9a-trans-2,9-Dimethyl-1,2,3,4,4a,9a-hexahydropyrido[3,4-b]indole 1,2,3,4-Tetrahydro-$\beta$-carboline (2.35 g) and NaH (60% nujol, 1.20 g) were added to anhydrous DMF and stirred at room temperature for 30 minutes. To the ice-cooled reaction solution was added methyl iodide (1.7 ml) and the reaction solution was stirred overnight. After removal of DMF by evaporation, the residue was mixed with water and extracted with chloroform. The extract was washed with water and dried over sodium sulfate. The crude product was purified by column chromatography on silica gel. Eluates with 5% methanol/chloroform afforded 1.6 g of 2,9-dimethyl-1,2,3,4-tetrahydro-$\beta$-carboline.

After addition of BF$_3$ ethyl ether complex (3.0 ml) to a solution of NaBH$_4$ (0.91 g) in THF under ice-cooling, 2,9-dimethyl-1,2,3,4-tetrahydro-$\beta$-carboline (0.8 g) as prepared above was added and the mixture was stirred for 30 minutes. Water was added to decompose excess borane, then trifluoroacetic acid (10 ml) was added and the mixture was stirred overnight at room temperature. The reaction solution was placed into an aqueous NaOH solution to make it basic, extracted with chloroform and dried over sodium sulfate. The crude product was purified by column chromatography on silica gel. Eluates with 10% methanol/chloroform afforded 0.69 g of the oily title compound.

PMR (CDCl$_3$, $\delta$) 1.71–1.81 (1H, m), 2.14–2.27(3H, m), 2.43–2.49(4H, m), 2.69–2.72(4H, m), 3.03(1H, d, J=11.7 Hz), 3.28(1H, dd, J=9.7, 2.9 Hz), 6.64(1H, d, J=7 Hz), 6.78(1H, t, J=7 Hz), 7.05–7.18(2H, m).

(2)

4a,9a-cis-2,9-Dimethyl-1,2,3,4,4a,9a-hexahydro-$\beta$-pyrido[3,4-b]indole 2,9-Dimethyl-1,2,3,4-tetrahydro-$\beta$-carboline (0.8 g) obtained in (1) was dissolved in trifluoroacetic acid, NaBH$_4$ (1.06 g) was added under ice-cooling and the mixture was stirred overnight. The reaction solution was placed into an aqueous NaOH solution to make it basic, extracted with chloroform and dried over sodium sulfate. The crude product was purified by column chromatography on silica gel. Eluates with 10% methanol/chloroform gave 0.57 g of the oily title compound.

PMR (CDCl$_3$, $\delta$) 1.64–1.71(1H, m), 1.87–1.91(1H, m), 2.07(1H, dt, J=8.0, 2.9 Hz), 2.28–2.30(1H, m), 2.31(3H, s), 2.58–2.63(1H, m), 2.76(3H, s), 2.91–3.00(2H, m), 3.21–3.25(1H, m), 6.55(1H, d, J=7 Hz), 6.72(1H, t, J=7 Hz), 7.06–7.12(2H, m).

(3)

2-Ethyl-9-(2,2,2-trifluoroethyl)-1,2,3,4,4a,9a-hexahydro-pyrido[3,4-b]indole (1) and 2-ethyl-1,2,3,4,4a,9a-hexahydro-pyrido[3,4-b]indole (2)

Ethyl iodide (2.4 ml) was added to a solution of 1,2,3,4-tetrahydro-9H-pyrido[3,4-b]indole (5.17 g) and sodium hydrogencarbonate (3.0 g) in 50 ml of acetonitrile and the solution was stirred at 70° C. over a bath for 3 hrs. After removal of the solvent by evaporation, water (60 ml) was added and the solution was extracted with chloroform. The extract was washed with brine and dried over magnesium sulfate. Purification of the crude product by silica gel column chromatography and crystallization from ethyl acetate of the eluates with methanol/chloroform ($\frac{1}{4}$) gave 1.5 g of 2-ethyl-1,2,3,4-tetrahydro-9H-pyrido[3,4-b]indole.

NaBH$_4$ (1.51 g) was added under ice-cooling to a solution of 2-ethyl-1,2,3,4-tetrahydro-9H-pyrido[3,4-b]indole (1.60 g) in 50 ml of trifluoroacetic acid. The solution was stirred at room temperature for 3 hrs and the solvent was evaporated off. The residue was neutralized with ammonia, extracted with chloroform, washed with brine and dried over magnesium sulfate.

The crude product was purified by column chromatography on silica gel. Eluates with methanol/chloroform (1/5) gave 0.68 g of 2-ethyl-9-(2,2,2-trifluoroethyl)-1,2,3,4,4a,9a-hexahydro-pyrido[3,4-b]indole (1) as an oily product and then 1.16 g of 2-ethyl-1,2,3,4,4a,9a-hexahydro-pyrido[3,4-b]indole (2).

(1) PMR (CDCl$_3$, $\delta$) 1.08(3H, t, J=7.2 Hz), 1.90(2H, m), 2.3–2.6(6H, m), 3.20(1H, dd, J=12.6, 5.7 Hz), 3.70(3H, m), 6.55(1H, d, J=7.6 Hz), 6.77(1H, t, J=7.4 Hz), 7.10(2H, m).

(2) PMR (CDCl$_3$, $\delta$) 1.09(3H, t, J=7.2 Hz), 2.00(2H, m), 2.2–2.6(6H, m), 3.20(1H, dd, J=12.6, 6.9 Hz), 3.88(1H, dd, J=13.1, 6.8 Hz), 6.67(1H, d, J=7.4 Hz), 6.76(1H, t, J=7.5 Hz), 7.10(2H, m).

(4) 2,9-Diethyl-1,2,3,4,4a,9a-hexahydro-pyrido[3,4-b]indole

NaBH$_4$ (1.08 g) was added under ice-cooling to a solution of 2-ethyl-1,2,3,4,4a,9a-hexahydro-pyrido[3,4-b]indole (1.16 g) in 40 ml of acetic acid. After stirring the solution at room temperature for 4 hrs, additional NaBH$_4$ (0.54 g) was added and the mixture was stirred for 3 hrs. After removal of acetic acid by evaporation, the residue was neutralized with ammonia, extracted with ethyl acetate, washed with brine and dried over magnesium sulfate. The solvent was evaporated off, thereby affording 1.26 g of the title compound as a pale yellow oil.

PMR (CDCl$_3$, δ) 1.11(6H, m), 1.7-2.5(7H, m), 2.65(1H, dd, J=12.2, 5.4 Hz), 3.12(2H, m), 3.39(1H, m), 3.64(1H, m), 6.47(1H, d, J=7.3 Hz), 6.66(1H, t, J=7.4 Hz), 7.05(2H, m).

(5) The following compounds (II) were synthesized from the corresponding 1,2,3,4-tetrahydro-β-carboline using the manners mentioned in (1)-(4).

| Compound | Appearance M.P. | PMR (CDCl$_3$, δ) |
|---|---|---|
| (indole-N-Me, side chain NEt) | Oil | 1.69(1H, m), 1.89(1H, m), 2.12(1H, dt, J=3.4, 12.8Hz), 2.32(1H, dd, J=12.7, 3.9 Hz), 2.45(2H, q, J=6.8Hz), 2.65(1H, m), 2.75(3H, s), 3.00(2H, m), 3.37(1H, m), 6.53(1H, d, J=7.9Hz), 6.70(1H, t, J=7.4 Hz), 7.10(2H, m) |
| (indole-N-Me, side chain NCH$_2$Ph) | Oil | 1.83(2H, m), 2.25(1H, m), 2.37(1H, dd, J=12.7, 3.9Hz), 2.60(1H, m), 2.63(3H, s), 2.80(1H, dd, J=12.7, 4.4Hz), 3.05(1H, m), 3.25(1H, m), 3.49(1H, d, J=13.2Hz), 3.64(1H, d, J=13.1Hz), 6.52(1H, d, J=7.8 Hz), 6.70(1H, t, J=7.3Hz), 7.10(2H, m), 7.30(5H, m) |
| (fused piperidine, N-Me) | 90-93° C. | 1.2-2.2(11H, m), 2.81(1H, dt, J=11.3, 3.4Hz), 2.91(3H, s), 3.05(3H, m), 6.63 (1H, d, J=7.8Hz), 6.73(1H, t, J=7.3Hz), 7.05(2H, m) |
| (N-Me, NMe, Me) | Oil | 1.43(3H, d, J=6.3Hz), 1.78-1.90(1H, m), 2.20-2.30(1H, m), 2.39(3H, s), 2.88 (3H, s), 2.4-2.5(3H, m), 2.7(1H, m), 3.05-3.12(1H, m), 6.66(1H, d, J=7Hz), 6.80(1H, t, J=7Hz), 7.04-7.17(2H, m) |
| (N-Me, NMe, Et) | Oil | 1.02(3H, t, J=7.5Hz), 1.76-1.86(1H, m), 1.94-1.98(2H, m), 2.19-2.23(1H, m), 2.34(3H, s), 2.44-2.51(2H, m), 2.67-2.77(2H, m), 2.88(3H, s), 6.66(1H, d, J=7 Hz), 6.79(1H, t, J=7Hz), 7.05(1H, d, J=7 Hz), 7.14(1H, t, J=7Hz) |
| (N-H, NEt, CH$_2$CH$_2$Ph) | Oil | 1.08(3H, t, J=7.Hz), 1.66-1.85(1H, m), 1.90-1.99(1H, m), 2.07-2.17(1H, m), 2.23-2.27(1H, m), 2.50-2.94(7H, m), 3.13-3.29(2H, m), 6.73(1H, d, J=7Hz), 6.80(1H, t, J=7Hz), 7.04-7.33(7H, m) |
| (N-Et, NEt, CH$_2$CH$_2$Ph) | Oil | 1.06(3H, t, J=7.Hz), 1.13(3H, t, J=7Hz), 1.64-1.74(1H, m), 1.82-2.06(3H, m), 2.62-3.13(8H, m), 3.16-3.26(3H, m), 6.57(1H, d, J=7Hz), 6.71(1H, t, J=7Hz), 7.02-7.30(7H, m) |

-continued

| Compound | Appearance M.P. | PMR (CDCl₃, δ) |
|---|---|---|
| (indoline with NEt, H, and CH₂CH₂Ph substituents) | Oil | 1.11(3H, t, J=7Hz), 1.16(3H, t, J=7Hz), 1.68-1.87(1H, m), 2.05-2.22(3H, m), 2.64-3.05(8H, m), 3.18-3.29(2H, m), 3.37-3.47(1H, m), 6.61(1H, d, J=7Hz), 6.76(1H, t, J=7Hz), 7.04(1H, d, J=7Hz), 7.11(1H, t, J=7Hz), 7.18-7.32(5H, m) |
| (OMe-substituted indoline with NMe, NMe) | Oil | 6.74(3H, s), 3.81(3H, s), 3.25(1H, m), 3.13(1H, m), 2.94(3H, s), 2.73(1H, m), 2.60(1H, m), 2.24(4H, m), 2.05(1H, m), 1.92(1H, m), 1.76(1H, t, J=11.2Hz) |
| (Cl-substituted indoline with NMe, NEt) | Oil | 7.03(1H, d, J=7.8Hz), 6.92(1H, d, J=6.8 Hz), 6.61(1H, t, J=7.8Hz), 3.92(1H, m), 3.58(1H, m), 3.30(1H, m), 3.23(1H, m), 2.66(1H, m), 2.56(1H, m), 2.30-2.15 (4H, m), 2.05(1H, m), 1.93(1H, m), 1.82 (1H, t-like, J=10.8Hz), 1.08(3H, t, J=7.3 Hz) |
| (Me-substituted indoline with NMe, NEt) | Oil | 6.91(1H, d, J=6.8Hz), 6.86(1H, d, J=6.3 Hz), 6.65(1H, t, J=7.8Hz), 3.59-3.49 (2H, m), 3.26(2H, m), 2.66(1H, m), 2.56 (1H, m), 2.36(3H, s), 2.28-2.10(4H, m), 2.00(2H, m), 1.85(1H, t-like, J=11.2Hz) |
| (indoline with NMe, NEt) | Oil | 7.14-7.04(2H, m), 6.66(1H, t, J=7.0Hz), 6.51(1H, d, J=8.0Hz), 3.56-3.46(1H, m), 3.29(1H, sex, J=7.0Hz), 3.22-3.04(2H, m), 2.74-2.66(1H, m), 2.56-2.48(1H, m), 2.26-2.16(4H, m), 1.96-1.86(3H, m), 1.08(3H, t, J=7.0Hz) |
| (indoline with NMe, N-CH₂Ph) | Oil | 7.38(2H, d, J=6.0Hz), 7.32(2H, t, J=8.0 Hz), 7.28-7.18(1H, m), 7.09(1H, d, J= 7.0Hz), 7.03(1H, t, J=7.0Hz), 6.70(1H, t, J=7.5Hz), 6.43(1H, d, J=8.0Hz), 4.24 (2H, dd, J=15.0, 6.0Hz), 3.58-3.50(1H, m), 3.30-3.20(1H, m), 2.80-2.70(1H, m), 2.56-2.46(1H, m), 2.30-2.20(4H, m), 2.06-1.84(3H, m) |
| (indoline with NMe, NMe) | Oil | 7.12(1H, t, J=7.5Hz), 7.08(1H, d, J=7.5 Hz), 6.72(1H, t, J=7.5Hz), 6.57(1H, d, J= 8.0Hz), 3.26-3.14(2H, m), 2.76-2.70 (1H, m), 2.69(3H, s), 2.62-2.54(1H, m), 2.25(3H, s), 2.24-2.14(1H, m), 2.06-1.80(3H, m) |
| (indoline with NMe, N-Me) | Oil | 7.14(1H, t, J=7.0Hz), 7.03(1H, d, J=7.5 Hz), 6.67(1H, t, J=7.5Hz), 6.63(1H, d, J= 8.0Hz), 3.45(1H, dd, J=11.0, 3.5Hz), 3.06(1H, d, J=12.0Hz), 2.89(1H, t, J=11.0 Hz), 2.71(3H, s), 2.42(3H, s), 2.42-2.34(1H, m), 2.24-2.00(3H, m), 1.90-1.80(1H, m) |
| (indoline with NEt, NEt) | Oil | 7.16-7.04(2H, m), 6.65(1H, t, J=7.5Hz), 6.51(1H, d, J=8.0Hz), 3.56-3.50(1H, m), 3.29(quintet, 1H, J=7.5Hz), 3.20-3.04 (2H, m), 2.80-2.74(1H, m), 2.66-2.60 (1H, m), 2.36(2H, q, J=7.0Hz), 2.24-2.16(1H, m), 2.04-1.84(3H, m), 1.08 (6H, t, J=7.5Hz) |

-continued

| Compound | Appearance M.P. | PMR (CDCl₃, δ) |
|---|---|---|
| ![structure with NEt] | Oil | 7.11(1H, t, J=8.0Hz), 7.06(1H, d, J=7.0 Hz), 6.72(1H, t, J=7.0Hz), 6.60(1H, d, J=8.0Hz), 3.54(1H, d, J=7.5Hz), 3.32–3.18(3H, m), 2.83(1H, t, J=13.0Hz), 2.71 (1H, t, J=8.0Hz), 2.64–2.50(2H, m), 2.20–2.00(3H, m), 2.57(1H, q, d, J=7.0, 3.0Hz), 1.16(3H, t, J=7.5Hz), 1.11(3H, t, J=7.5Hz) |
| ![structure with NCH₂Ph] | Oil | 7.36–7.20(5H, m), 7.08(1H, t, J=8.0Hz), 6.98(1H, d, J=7.5Hz), 6.63(1H, t, J=7.5 Hz), 6.51(1H, d, J=7.0Hz), 3.56–3.50 (1H, m), 3.44(2H, s), 3.25(sex, 1H, J=7.0Hz), 3.20–3.04(2H, m), 2.76–2.66 (1H, m), 2.62–2.54(1H, m), 2.30–2.20 (1H, m), 2.00–1.84(3H, m), 1.07(3H, t, J=7.5Hz) |
| ![structure with NCH₂Ph] | Oil | 7.40–7.18(5H, m), 7.08(1H, t, J=7.5Hz), 6.97(1H, d, J=7.5Hz), 6.68(1H, t, J=8.0 Hz), 6.58(1H, d, J=8.0Hz), 3.66(2H, s), 3.30–3.10(2H, m), 3.06(1H, d, J=12.0 Hz), 2.86(1H, t, J=11.0Hz), 2.76–2.62 (1H, m), 2.24–2.08(2H, m), 2.04–1.76 (3H, m), 1.09(3H, t, J=7.0Hz) |

REFERENTIAL EXAMPLE 2

Synthesis of 6-formyl-2,9-diethyl-1,2,3,4,4a,9a-tetrahydropyrido[3,4-b]indole (III)

Phosphorus oxychloride (0.56 ml) was added under ice-cooling to DMF (10 ml) and the solution was stirred for one hour. Then a solution of 2,9-diethyl-1,2,3,4,4a,9a-tetrahydro-pyrido[3,4-b]indole (1.15 g) in DMF (10 ml) was added and the mixture was stirred at room temperature for 5 hrs. The reaction solution was poured into an aqueous sodium hydrogencarbonate solution to neutralize and extracted with ethyl acetate. The extract was washed with water and brine and dried over magnesium sulfate. The crude product was purified by column chromatography on silica gel. Eluates with 3% methanol/chloroform gave 1.07 g of the oily title compound.

PMR (CDCl₃, δ) 1.09(3H, t, J=7.3 Hz), 1.19(3H, t, J=7.3 Hz), 1.88(1H, m), 2.00(1H, m), 2.3–2.6(6H, m), 3.21(2H, m), 3.46(1H, m), 3.84(1H, q, J=6.3 Hz), 6.46(1H, d, J=8.3 Hz), 7.57(2H, m), 9.69(1H, s).

REFERENTIAL EXAMPLE 3

Synthesis of Compound (IV)

(1) 8-Ethoxy-3-ethoxycarbonyl-1,2,3,4,5,6,7,8-octahydroazecino[5,4-b]indole

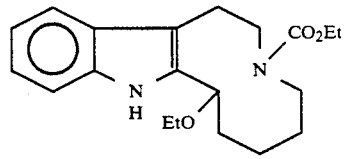

To chloroform (115 ml) were added indoloquinolizine (1.12 g), sodium carbonate (2.49 g), EtOH (3.22 g) and ethyl chloroformate (1.63 g) and the mixture was stirred at room temperature for 7 hrs. The insoluble material was filtered off, the filtrate was washed with water and the brine, dried over magnesium sulfate, and the solvent was evaporated off. Purification of the crude product by silica gel column chromatography and recrystallization from n-hexane of the eluates with chloroform/ethyl acetate (20/1) afforded 1.25 g of the title compound.

M.P. 137°–139° C.

PMR (CDCl₃, δ) 0.6–2.19(12H, m), 2.42–4.60(11H, m), 7.02–7.25(2H, m), 7.36(1H, d, J=7 Hz), 7.51(1H, d, J=7 Hz), 8.38(1H, brs).

(2) The following compounds were prepared from the corresponding starting materials in a similar manner as mentioned above.

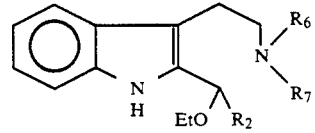
(IV)

| R₂, R₇ | R₆ | Appearance M.P. | PMR (CDCl₃, δ) |
|---|---|---|---|
| —(CH₂)₄— | CO₂CH₂Ph | Amorphous solid | 1.15(3H, t, J=6.8Hz), 1.41(3H, m), |

-continued

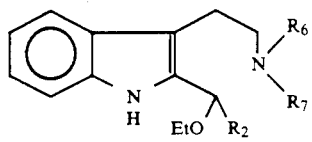
(IV)

| $R_2$, $R_7$ | $R_6$ | Appearance M.P. | PMR (CDCl$_3$, δ) |
|---|---|---|---|
| | | | 1.73(1H, m), 2.05(1H, m), 2.90(2H, m), 3.05-3.70(5H, m), 3.97(1H, m), 4.40(1H, m), 4.75(1H, m), 5.15(2H, m), 7.00-7.25(3H, m), 7.35(5H, m), 7.50(1H, m), 8.35(1H, brs) |
| —(CH$_2$)$_4$— | CO$_2$CH$_2$CCl$_3$ | Amorphous solid | 1.43(3H, m), 1.75(1H, m), 2.05(1H, m), 2.7-3.1(4H, m), 3.20(2H, s), 3.25-3.7(3H, m), 4.0-4.3(2H, m), 4.39(1H, m), 4.65(1H, d, J=11.4Hz), 4.8(1H, d, J=11.4Hz), 4.99(1H, d, J=14.9Hz), 7.05-7.25(2H, m), 7.35 (1H, d, J=6.9Hz), 7.52(1H, d, J=6.9 Hz), 8.35(1H, brs) |
| —(CH$_2$)$_3$— | CO$_2$Et | 167-171° C. | 0.72-0.88(1H, m), 1.17(3H, t, J=7 Hz), 1.35(3H, t, J=7Hz), 1.70-1.85 (1H, m), 2.07-2.24(1H, m), 2.45-2.67(2H, m), 2.90-3.20(2H, m), 3.36-3.50(2H, m), 3.89-4.41(4H, m), 4.65-4.74(1H, m), 7.08-7.23(2H, m), 7.32-7.40(1H, m), 7.55(1H, t, J=8Hz), 8.21, 8.28(each 0.5H, brs) |
| —(CH$_2$)$_3$— | CO$_2$CH$_2$Ph | 198-201° C. | 0.72-0.87(1H, m), 1.11(3H, dd, J=14.1, 7.3Hz), 1.29-1.42(1H, m), 1.68-1.80(1H, m), 2.04-2.21(1H, m), 2.49-2.70(2H, m), 2.93-3.36 (4H, m), 3.96-4.18(2H, m), 4.56-4.65(1H, m), 5.12-5.17(1H, m), 5.30-5.39(1H, m), 7.11-7.19(2H, m), 7.31-7.57(7H, m), 8.10, 8.16(each 0.5H, brs) |
| —CH$_2$—⟨phenyl⟩—CH$_2$— | CO$_2$Et | Amorphous solid | 1.13(3H, brt), 1.24(3H, t, J=6.8Hz), 2.92(3H, m), 3.21(2H, m), 3.47(3H, m), 3.70-4.20(3H, m), 4.68(1H, m), 4.85(1H, m), 6.90-7.41(8H, m), 8.19 (1H, brs) |
| —CH$_2$—⟨phenyl⟩—CH$_2$— | CO$_2$CH$_2$Ph | Amorphous solid | 1.21(3H, t, J=7.8Hz), 2.60-3.60(8H, m), 3.65-4.20(2H, m), 4.75(2H, m), 5.15(1H, m), 6.80-7.20(6H, m), 7.30 (7H, m), 8.15(1H, brs) |
| Me, —CH$_2$Ph | CO$_2$Et | Oil | 1.15(3H, t, J=6.9Hz), 1.30(3H, m), 1.48(3H, d, J=6.4Hz), 2.87(2H, m), 3.32(4H, m), 4.0-4.8(5H, m), 7.0-7.5(9H, m), 8.38(1H, brs) |
| Me, —CH$_2$Ph | CO$_2$CH$_2$Ph | Oil | 1.10(3H, m), 1.3-1.5(3H, m), 2.80 (1H, m), 2.95(1H, m), 3.15(1H, m), 3.2-3.6(3H, m), 4.3-4.7(2H, m), 5.23(2H, s), 6.90-7.50(14H, m), 8.10(1H, m) |
| Me, Et | CO$_2$CH$_2$Ph | Oil | 1.05-1.35(9H, m), 1.54(3H, d, J=6.9 Hz), 3.00(2H, m), 3.1-3.5(6H, m), 4.19(2H, m), 4.80(1H, m), 7.15(2H, m), 7.36(1H, d, J=7.3Hz), 7.60(1H, m), 8.51(1H, brs) |

REFERENTIAL EXAMPLE 4

Synthesis of Compound (V)

(1) 1-Tosyl-N,N-dibenzyl-tryptamine

N,N-dibenzyl-tryptamine (1.70 g) and tetra-n-butyl ammonium hydrogensulfate (0.17 g) in benzene (5 ml) were added to 50% aqueous NaOH solution (5 ml) and tosyl chloride (1.43 g) and the mixture was stirred at room temperature for 2 hrs. The organic layer was separated, washed with water and then brine and dried over magnesium sulfate. The solvent was evaporated off. Crystallization from acetone/hexane afforded 1.83 g of the title compound.

M.P. 116°-118° C.

PMR (CDCl$_3$, δ)2.30(3H, s), 2.76(2H, m), 2.83(2H, t, J=7.3 Hz), 3.64(4H, s), 7.05-7.35(16H, m), 7.71(2H, m), 7.93(1H, d, J=8.3 Hz).

(2) 3-(2-(2-pyridyl)ethyl)-1-tosyl-indole

In a similar manner, the title compound was prepared from the corresponding starting material.

PMR (CDCl₃, δ) 2.33(3H, s), 3.14(4H, m), 7.04(1H, d, J=7.8 Hz), 7.1-7.3(6H, m), 7.49(1H, d, J=7.8 Hz), 7.54(1H, td, J=7.8, 1.9 Hz), 7.67(2H, d, J=8.3 Hz), 7.96(1H, d, J=8.3 Hz), 8.57(1H, dd, J=4.9, 0.9 Hz).

(3) 1-Methyl-N,N-dibenzyl-tryptamine

N,N-dibenzyl-tryptamine (1.72 g) was added to an anhydrous DMF solution containing 0.24 g of NaH (60% nujol) and the mixture was stirred for 15 minutes. Methyl iodide (0.31 ml) was added and the mixture was stirred for one hour. Water was added and the solvent was evaporated off. The residue to which water was added was extracted with IPE, the extract was washed with water and the brine and dried over magnesium sulfate. The crude product was purified by column chromatography on silica gel. Eluates with ethyl acetate/hexane (1/9) afforded 1.58 g of the oily title compound.

PMR (CDCl₃, δ) 2.79(2H, dd, J=10.3, 7.3 Hz), 2.95(2H, dd, J=10.3, 6.9 Hz), 3.69(7H, s), 6.72(1H, s), 7.01(1H, m), 7.2-7.4(13H, m).

(4) In a similar manner, the following compounds were prepared from the corresponding starting materials.

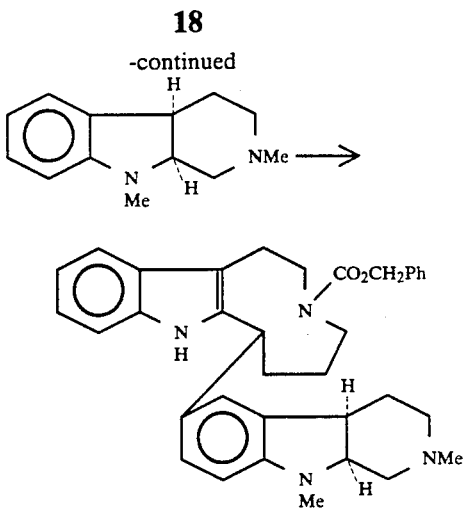

3-Benzyloxycarbonyl-7-ethoxy-1,2,4,5,6,7-hexahydro-3H-azonino[5,4-b]indole (1.1 g) and 4a,9a-cis-2,9-dimethyl-1,2,3,4,4a,9a-hexahydro-pyrido[3,4-b]indole (0.55 g) were heated at reflux in an ethanol solution containing 1.5% HCl. After two hours, the reaction

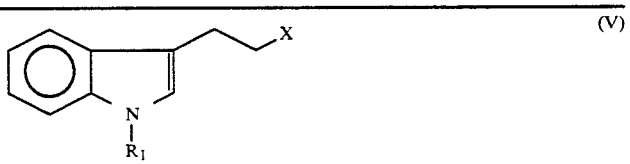

| R₁ | X | Appearance | PMR (CDCl₃, δ) |
|---|---|---|---|
| —CH₂Ph | —N(CH₂Ph)₂ | Oil | 2.81(2H, dd, J=8.3, 5.9Hz), 2.98(2H, t, J=7.3Hz), 3.67(4H, s), 5.22(2H, s), 6.83(1H, s), 7.01(1H, t, J=7.8Hz), 7.10(3H, m), 7.25(11H, m), 7.37(4H, m) |
| —CH₂Ph | —OCH₂Ph | Oil | 3.10(2H, t, J=6.9Hz), 3.78(2H, t, J=7.3Hz), 4.55(2H, s), 5.26(2H, s), 6.97(1H, s), 7.10-7.20(4H, m), 7.20-7.35(9H, m), 7.60(1H, d, J=7.8Hz) |
| —Me | —OCH₂Ph | Oil | 3.08(2H, t, J=7.3Hz), 3.73(3H, s), 3.76(2H, t, J=7.3Hz), 4.56(2H, s), 6.90(1H, s), 7.09(1H, t, J=7.8Hz), 7.15-7.35(7H, m), 7.58(1H, d, J=8.3Hz) |

EXAMPLE 1

4a,9a-cis-6-(3-Benzyloxycarbonyl-1,2,4,5,6,7-hexahydro-3H-azonino[5,4-b]indole-7-yl)-2,9-dimethyl-1,2,3,4,4a,9a-hexahydro-pyrido[3,4-b]indole

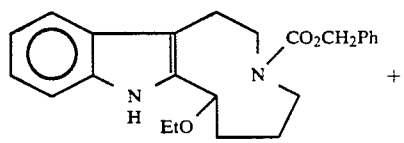

solution was treated with sodium hydrogencarbonate to make it basic, extracted with chloroform, dried over anhydrous sodium sulfate and the solvent was evaporated off. The crude product was purified by column chromatography on silica gel. Eluates with 5% methanol/chloroform gave 1.49 g of the title compound.

Amorphous Solid

PMR (CDCl₃, δ) 0.98-1.18(1H, m), 1.37-1.92(4H, m), 1.99-2.39(6H, m), 2.58-3.38(11H, m), 4.00-4.22(2H, m), 4.34-4.49(1H, m), 5.02-5.37(2H, m), 6.45-6.59(1H, m), 6.82-7.60(11H, m).

EXAMPLES 2-33

In a similar manner, the following compounds were prepared from the corresponding starting materials.

(I)

| Example No. | $R_2$, $R_7$ | $R_6$ | A | Appearance | PMR (CDCl$_3$, δ) |
|---|---|---|---|---|---|
| 2 | —(CH$_2$)$_4$— | CO$_2$Et | (indoline with NMe) | Amorphous solid | 0.9–1.3(10H, m), 1.60(2H, m), 2.06(4H, m), 2.29(1H, dd, J=12.0, 4.0Hz), 2.45(2H, q, J=7.4Hz), 2.71(3H, m), 2.91(2H, m), 3.20(4H, m), 3.75(2H, m), 3.91(1H, m), 4.15(2H, m), 6.48(1H, brs), 6.82(1H, m), 7.07(4H, m), 7.50(2H, m) |
| 3 | —(CH$_2$)$_4$— | CO$_2$CH$_2$Ph | (indoline with NEt) | Amorphous solid | 1.12(6H, m), 1.7–1.4(4H, m), 2.3–1.8(5H, m), 2.3–2.8(6H, m), 2.9–3.5(6H, m), 3.5–4.0(3H, m), 4.10(1H, m), 5.10(2H, m), 6.40(1H, m), 6.8–7.5(12H, m) |
| 4 | —(CH$_2$)$_4$— | CO$_2$Et | (indoline with NEt) | Amorphous solid | 0.9–1.3(10H, m), 1.85(2H, m), 2.05(2H, m), 2.25(2H, m), 2.40(4H, m), 2.65(2H, m), 2.9–3.5(7H, m), 3.35–3.50(3H, m), 3.92(1H, m), 4.15(2H, m), 6.40(1H, dd, J=12.6, 6.9Hz), 6.80(1H, brs), 7.05(4H, m), 7.50(2H, m) |
| 5 | —(CH$_2$)$_4$— | CO$_2$Et | (indoline with NCH$_2$CF$_3$) | Amorphous solid | 1.0–1.3(8H, m), 1.58(4H, m), 2.05(2H, m), 2.2–2.6 (4H, m), 2.9–3.4(6H, m), 3.71(4H, m), 4.12(2H, m), 6.49(1H, m), 6.85(1H, m), 7.05(4H, m), 7.40(2H, m) |
| 6 | —(CH$_2$)$_4$— | CO$_2$Et | (indoline with NMe, CH$_2$Ph) | Amorphous solid | 1.0(3H, brt), 1.29(2H, m), 1.4–1.9(4H, m), 2.11(3H, m), 2.32(1H, m), 2.61(3H, s), 2.89(1H, m), 3.20(6H, m), 3.48(1H, d, J=14.9Hz), 3.62(1H, m), 3.80(2H, m), 3.92(1H, m), 4.15(2H, m), 6.46(1H, m), 6.8–7.2 (5H, m), 7.2–7.6(7H, m) |

-continued (I)

[Structure: indole with NH, attached to C=C bearing R2 and A groups, with CH2-N(R6)(R7) substituent]

| Example No. | R2, R7 | R6 | A | Appearance | PMR (CDCl3, δ) |
|---|---|---|---|---|---|
| 7 | —(CH2)4— | CO2Et | [2-(N-methyl)piperidinyl-methyl on tolyl: N-Me indoline-like with piperidine] | Amorphous solid | 1.0(3H, brt), 1.21(2H, m), 1.4-2.3(15H, m), 2.79(1H, m), 2.88(3H, m), 2.95(2H, m), 3.05-3.35(4H, m), 3.75 (2H, m), 3.90(1H, m), 4.15(2H, m), 6.55(1H, m), 6.80 (1H, brs), 7.05(4H, m), 7.49(2H, m) |
| 8 | —(CH2)4— | CO2CH2CCl3 | [NEt piperidinyl on N-Et indoline/tolyl] | Amorphous solid | 1.10(6H, m), 1.8-4.2(24H, m), 4.70(2H, m), 4.90(1H, d, J=6.3Hz), 6.40(2H, m), 6.80(1H, m), 6.95(1H, m), 7.08 (2H, m), 7.18(1H, m), 7.51(1H, m) |
| 9 | —CH2-C6H4-CH2— (o-xylylene) | CO2Et | [NEt piperidinyl on N-Et tolyl] | Amorphous solid | 0.75(3H, m), 1.15(6H, m), 1.6-2.1(4H, m), 2.2-2.6 (6H, m), 2.70(2H, m), 2.9-3.3(3H, m), 3.3-3.5(3H, m), 3.5-3.9(2H, m), 4.0-4.6(3H, m), 6.50(1H, m), 6.8-7.3(10H, m), 7.40(1H, m) |
| 10 | —CH2-C6H4-CH2— (o-xylylene) | CO2CH2Ph | [NEt piperidinyl on N-Et tolyl] | Amorphous solid | 1.11(6H, m), 1.96(2H, m), 2.15-2.60(6H, m), 2.70(2H, m), 3.10(3H, m), 3.40(3H, m), 3.68(3H, m), 4.43(2H, m), 4.7-5.2(2H, m), 6.49(2H, m), 6.65(1H, t, J=8.6Hz), 6.8-7.3(12H, m), 7.36(2H, m) |
| 11 | —(CH2)3— | CO2CH2Ph | [NEt piperidinyl on N-Et tolyl] | Amorphous solid | 1.11(6H, m), 1.45(1H, m), 1.7-2.0(3H, m), 2.05-2.35 (3H, m), 2.40(4H, m), 2.70(1H, m), 2.85(2H, m), 2.9-3.2(3H, m), 3.2-3.5(2H, m), 3.62(1H, m), 4.0-4.2(2H, m), 4.40(1H, m), 5.10(1H, m), 5.28(1H, m), 6.40(1H, m), 6.8-7.05(2H, m), 7.05-7.25(4H, m), 7.25(3H, m), 7.4 (1H, m), 7.55(2H, m) |

-continued (I)

| Example No. | $R_2, R_7$ | $R_6$ | A | Appearance | PMR (CDCl$_3$, δ) |
|---|---|---|---|---|---|
| 12 | —(CH$_2$)$_3$— | CO$_2$CH$_2$Ph | (structure with NMe, N-Me, phenyl) | Amorphous solid | 1.00–1.15(1H, m), 1.20–1.34(1H, m), 1.67–1.82(1H, m), 2.05–2.47(9H, m), 2.69–2.92(6H, m), 2.98–3.40(4H, m), 4.00–4.18(2H, m), 4.39–4.46(1H, m), 5.05–5.35(2H, m), 6.57–6.63(1H, m), 6.84–7.6(12H, m) |
| 13 | —(CH$_2$)$_3$— | CO$_2$CH$_2$Ph | (structure with NMe, Me, N-Me, phenyl) | Amorphous solid | 0.99–1.13(2.5H, m), 1.39–1.52(2.5H, m), 1.7–1.9(1H, m), 2.02–3.58(17H, m), 4.00–4.20(2H, m), 4.36–4.43(1H, m), 5.05–5.42(2H, m), 6.48–6.68(1H, m), 6.78–6.89(1H, m), 6.98–7.57(11H, m) |
| 14 | —(CH$_2$)$_3$— | CO$_2$CH$_2$Ph | (structure with NMe, Et, N-Me, phenyl) | Amorphous solid | 0.99–1.10(4H, m), 1.38–1.53(1H, m), 1.70–2.20(6H, m), 2.33(3H, s), 2.36–2.90(9H, m), 3.01–3.38(2H, m), 4.35–4.41(1H, m), 5.05–5.33(2H, m), 6.61(1H, t, J=7.8 Hz), 6.83(1H, d, J=13.7Hz), 6.95–7.68(11H, m) |
| 15 | —(CH$_2$)$_3$— | CO$_2$Et | (structure with NEt, N-Et, phenyl, Ph) | Amorphous solid | 0.95–1.54(12H, m), 1.70–1.85(1H, m), 1.90–2.35(4H, m), 2.48–3.50(15H, m), 3.89–4.30(4H, m), 4.34–4.49(1H, m), 6.48–6.62(1H, m), 6.82–7.35(10H, m), 7.47–7.69(2H, m) |
| 16 | —(CH$_2$)$_3$— | CO$_2$Et | (structure with NEt, Me, N-Et, phenyl, Ph) | Amorphous solid | 1.0–1.31(12H, m), 1.36–1.48(1H, m), 1.57–1.71(1H, m), 1.76–2.30(5H, m), 2.53–3.36(15H, m), 3.88–4.28(4H, m), 4.32–4.44(1H, m), 6.47–6.56(1H, m), 6.83–7.30(10H, m), 7.45–7.62(2H, m) |

-continued (I)

| Example No. | R$_2$, R$_7$ | R$_6$ | A | Appearance | PMR (CDCl$_3$, δ) |
|---|---|---|---|---|---|
| 17 | —(CH$_2$)$_3$— | CO$_2$Et | (structure: indoline with NEt and CH$_2$CH$_2$Ph substituents) | Amorphous solid | 0.95-1.52(9H, m), 1.60-2.33(5H, m), 2.40-3.39(13H, m), 3.75-4.30(5H, m), 4.33-4.58(1H, m), 6.60-6.72 (1H, m), 6.87-7.31(10H, m), 7.39-7.60(2H, m) |
| 18 | Me, —CH$_2$Ph | CO$_2$Et | (structure: indoline with NEt) | Amorphous solid | 1.10(6H, m), 1.30(3H, m), 1.60(3H, d, J=6.8Hz), 1.72 (1H, m), 1.85(1H, m), 2.23(1H, m), 2.41(4H, m), 2.65 (1H, m), 2.8-3.2(4H, m), 3.36(2H, m), 3.61(1H, m), 4.22(3H, m), 4.3-4.6(3H, m), 6.40(1H, m), 6.90(1H, m), 7.03(3H, m), 7.19(3H, m), 7.25(3H, m), 7.3-7.6(2H, m) |
| 19 | Me, —CH$_2$Ph | —CO$_2$CH$_2$Ph | (structure: N-Et indoline) | Amorphous solid | 1.09(6H, m), 1.47(2H, d, J=7.4Hz), 1.60(1H, d, J=7.4Hz), 1.70(2H, m), 1.85(1H, m), 2.20(1H, m), 2.40(4H, m), 2.61(1H, m), 2.75-3.15(4H, m), 3.2-3.5(3H, m), 3.60 (1H, m), 4.3-4.5(2H, m), 5.23(2H, s), 6.39(1H, m), 6.80(1H, m), 6.89(1H, m), 7.03(2H, m), 7.1-7.6 (13H, m) |
| 20 | Me, Et | —CO$_2$CH$_2$Ph | (structure: N-Et indoline) | Amorphous solid | 1.10(9H, m), 1.5-1.9(7H, m), 2.22(1H, m), 2.40(4H, m), 2.65(1H, m), 2.8-3.2(4H, m), 3.2-3.5(4H, m), 3.61 (1H, m), 5.16(2H, s), 6.40(1H, m), 6.85(1H, m), 6.95 (1H, m), 7.05(2H, m), 7.22(2H, m), 7.36(5H, m), 7.61 (1H, m) |
| 21 | Me, Et | CO$_2$Et | (structure: N-Et indoline) | Amorphous solid | 1.0-1.2(9H, m), 1.28(3H, t, J=7.3Hz), 1.65(3H, d, J=7.3 Hz), 1.7-2.0(7H, m), 2.2-2.5(5H, m), 2.70(2H, m), 2.9-3.5(8H, m), 3.63(1H, m), 4.17(2H, q, J=6.8Hz), 4.39(1H, m), 6.41(1H, m), 6.9-7.2(4H, m), 7.23(1H, m), 7.5-7.7(2H, m) |

-continued (I)

| Example No. | $R_2, R_7$ | $R_6$ | A | Appearance | PMR (CDCl$_3$, δ) |
|---|---|---|---|---|---|
| 22 | —(CH$_2$)$_3$— | CO$_2$CH$_2$Ph | (tetrahydroisoquinoline with NMe, N-Et, Me substituents) | Amorphous solid | 7.78–7.45(2H, m), 7.40(1H, m), 7.33–7.13(5H, m), 7.09(2H, m), 6.82–6.65(2H, m), 5.37–5.19(1H, m), 5.11(1H, m), 4.35(1H, m), 4.20–3.92(2H, m), 3.50(2H, m), 3.38–3.10(3H, m), 3.05(1H, m), 2.80(2H, m), 2.65–2.40(2H, m), 2.38–1.85(12H, m), 1.42(1H, m), 1.02(4H, m) |
| 23 | —(CH$_2$)$_3$— | CO$_2$CH$_2$Ph | (tetrahydroisoquinoline with NMe, N-Et, Cl substituents) | Amorphous solid | 7.60–7.44(2H, m), 7.40(1H, m), 7.32–7.13(5H, m), 7.10(2H, m), 6.90(1H, m), 6.70(1H, m), 5.32(1H, m), 5.09(1H, m), 4.39–4.00(2H, m), 3.92(1H, m), 3.57(1H, m), 3.36–2.94(3H, m), 2.80(2H, m), 2.58(2H, m), 2.31–2.11(6H, m), 2.11–1.75(5H, m), 1.42(1H, m), 1.09 (4H, m) |
| 24 | —(CH$_2$)$_3$— | CO$_2$CH$_2$Ph | (tetrahydroisoquinoline with NMe, N-Me, OMe substituents) | Amorphous solid | 7.6–7.5(2H, m), 7.40(1H, m), 7.31–7.12(5H, m), 7.09 (1H, m), 6.71, 6.63(1H, each s), 6.55(1H, m), 5.31, 5.26(1H, each dd, J=12.2, 4.9Hz, J=12.7, 4.4Hz), 5.10(1H, m), 4.40(1H, m), 4.17–3.99(2H, m), 3.71(3H, m), 3.34–3.04(4H, m), 2.92(3H, m), 2.82(2H, m), 2.72 (1H, m), 2.61(1H, m), 2.30–1.63(9H, m), 1.44(1H, m), 1.04(1H, m) |
| 25 | —(CH$_2$)$_3$— | CO$_2$CH$_2$Ph | (tetrahydroisoquinoline with NMe, N-Et, stereochem H) | Amorphous solid | 7.64–7.44(2H, m), 7.42–7.36(1H, m), 7.36–7.24(2H, m), 7.24–7.16(3H, m), 7.16–7.04(2H, m), 7.04–6.86 (3H, m), 6.50–6.42(1H, m), 5.36–5.04(2H, m), 4.46–4.28(1H, m), 4.20–3.92(2H, m), 3.92–3.80(1H, m), 3.76–3.66(1H, m), 3.58–3.48(1H, m), 3.20–2.95(5H, m), 2.38–1.75(10H, m), 1.50–1.34(1H, m), 1.16–0.82 (4H, m) |
| 26 | —(CH$_2$)$_3$— | CO$_2$CH$_2$Ph | (tetrahydroisoquinoline with NMe, N-Et, stereochem H) | Amorphous solid | 7.70–7.45(2H, m), 7.45–7.21(4H, m), 7.21–6.95(6H, m), 6.95–6.65(2H, m), 6.62–6.42(1H, m), 5.36–5.02 (2H, m), 4.45–4.30(1H, m), 4.20–3.97(2H, m), 3.56–2.95(6H, m), 2.45–1.78(11H, m), 1.55–1.34(1H, m), 1.16–0.95(4H, m) |

-continued (I)

| Example No. | $R_2$, $R_7$ | $R_6$ | A | Appearance | PMR (CDCl$_3$, δ) |
|---|---|---|---|---|---|
| 27 | —(CH$_2$)$_3$— | CO$_2$CH$_2$Ph | (structure with NMe, CH$_2$Ph) | Amorphous solid | 7.77–7.44(3H, m), 7.42–7.16(11H, m), 7.16–7.04(2H, m), 6.91(2H, t, J = 12.0Hz), 6.35(1H, t, J = 7.0Hz), 5.32–5.06(2H, m), 4.44–4.28(2H, m), 4.18–3.94(2H, m), 3.54–3.46(1H, m), 3.36–2.94(3H, m), 2.86–2.60(3H, m), 2.46–1.80(6H, m), 1.52–1.10(5H, m), 1.10–0.80 (2H, m) |
| 28 | —(CH$_2$)$_3$— | CO$_2$CH$_2$Ph | (structure with NMe, N-Me) | Amorphous solid | 7.58–7.46(2H, m), 7.42–7.38(2H, m), 7.34–7.24(3H, m), 7.24–7.16(2H, m), 7.12–6.85(4H, m), 6.52(1H, t, J = 8.0Hz), 5.36–5.06(2H, m), 4.46–4.30(1H, m), 4.20–3.95(2H, m), 3.35–3.05(3H, m), 2.86(2H, t, J = 13.5 Hz), 2.76–2.64(3H, m), 2.64–2.48(1H, m), 2.32–2.04 (6H, m), 2.04–1.88(2H, m), 1.84–1.75(1H, m), 1.52–1.34(1H, m), 1.14–0.96(1H, m) |
| 29 | —(CH$_2$)$_3$— | CO$_2$CH$_2$Ph | (structure with NEt, N-Et) | Amorphous solid | 7.60–7.46(2H, m), 7.42–6.84(11H, m), 6.52–6.44(1H, m), 5.36–5.06(2H, m), 4.46–4.32(1H, m), 4.20–3.96 (2H, m), 3.60–3.50(1H, m), 3.36–3.24(1H, m), 3.24–3.02(4H, m), 2.88–2.60(3H, m), 2.60–2.34(2H, m), 2.34–2.04(2H, m), 2.04–1.90(3H, m), 1.90–1.76(1H, m), 1.52–1.36(1H, m), 1.16–0.96(7H, m) |
| 30 | —(CH$_2$)$_3$— | CO$_2$CH$_2$Ph | (structure with NMe, N-Me) | Amorphous solid | 7.55–7.00(11H, m), 6.82(2H, s), 6.52–6.60(1H, m), 5.32–5.18(1H, m), 5.11(1H, t, J = 2.0Hz), 4.44–4.32 (1H, m), 4.20–3.95(2H, m), 3.45–3.23(2H, m), 3.22–3.00(2H, m), 2.92–2.75(3H, m), 2.71(3H, d, J = 4.0Hz), 2.42–2.20(1H, m), 2.40(3H, s), 2.18–2.03(4H, m), 1.94–1.78(1H, m) |
| 31 | —(CH$_2$)$_3$— | CO$_2$CH$_2$Ph | (structure with NEt, N-Et) | Amorphous solid | 7.60–6.76(13H, m), 6.60–6.46(1H, m), 5.36–5.18(1H, m), 5.10(1H, t, J = 12.0Hz), 4.46–4.34(1H, m), 4.24–3.96(2H, m), 3.54–3.44(1H, m), 3.38–3.00(5H, m), 2.90–2.46(5H, m), 2.36–2.24(1H, m), 2.24–1.96(4H, m), 1.94–1.76(1H, m), 1.54–1.36(1H, m), 1.20–0.96 (7H, m) |

-continued

| Example No. | $R_2, R_7$ | $R_6$ | A | Appearance | PMR (CDCl$_3$, δ) |
|---|---|---|---|---|---|
| 32 | —(CH$_2$)$_3$— | CO$_2$CH$_2$Ph | | Amorphous solid | 7.60–7.40(2H, m), 7.40–6.48(16H, m), 6.43(1H, t, J = 7.5Hz), 5.34–5.14(1H, m), 5.08(1H, t, J=6.0Hz), 4.44–4.24(1H, m), 4.16–3.88(2H, m), 3.58–3.36(3H, m), 3.36–3.18(1H, m), 3.18–2.94(3H, m), 2.90–2.40(4H, m), 2.40–1.76(6H, m), 1.46–1.30(1H, m), 1.14–0.86 (4H, m) |
| 33 | —(CH$_2$)$_3$— | CO$_2$CH$_2$Ph | | Amorphous solid | 7.60–7.44(2H, m), 7.44–6.84(15H, m), 6.82–6.70(1H, m), 6.60–6.40(1H, m), 5.36–5.16(1H, m), 5.16–5.04 (1H, m), 4.44–4.26(1H, m), 4.18–3.92(2H, m), 3.70–3.36(3H, m), 3.36–2.96(5H, m), 2.94–2.50(3H, m), 2.40–1.96(4H, m), 1.96–1.60(2H, m), 1.50–1.34(1H, m), 1.16–0.94(4H, m) |

EXAMPLE 34

2,9-Diethyl-6-(3-(2-dibenzylaminoethyl)-1-tosyl-indole-2-yl)hydroxymethyl-1,2,3,4,4a,9a-hexahydropyrido[3,4-b]indole

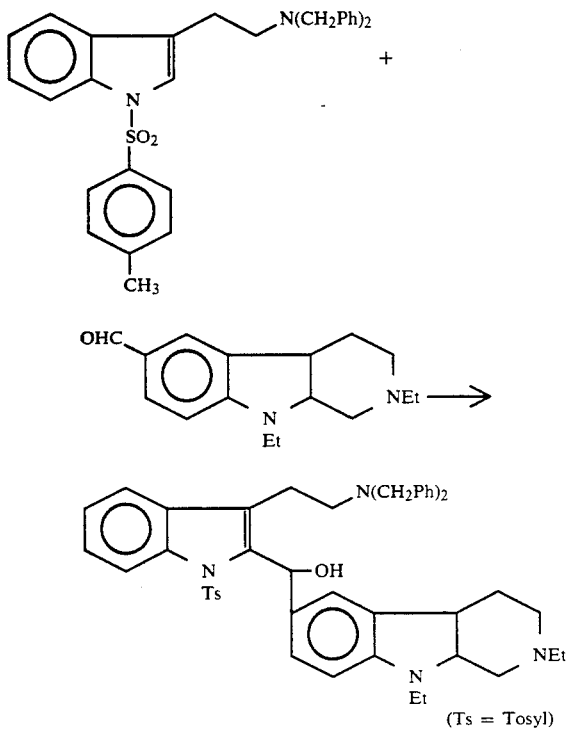

(Ts = Tosyl)

2.18 ml of n-BuLi (15% hexane) were added under ice-cooling to a solution of 1-tosyl-N,N-dibenzyltryptamine (1.72 g) in anhydrous THF, which was cooled with dry ice-acetone. 6-Formyl-2,9-dimethyl-1,2,3,4,4a,9a-hexahydropyrido[3,4-b]indole (0.6 g) was added and the mixture stirred for 4 hrs. Methanol was added and the solvent was removed by evaporation from the reaction solution. The residue to which water was added was extracted with ethyl acetate. The ethyl acetate layer was washed with water and then brine, dried over magnesium sulfate. The crude product was purified by column chromatography on silica gel. Eluates with 3% methanol/chloroform gave 1.15 g of the title compound.

Amorphous Solid

PMR (CDCl$_3$, δ) 1.10(6H, m), 1.65-1.95(3H, m), 2.24(3H, s), 2.40(4H, m), 2.60(4H, m), 2.82(1H, m), 2.99(1H, m), 3.10(1H, m), 3.32(1H, m), 3.50(2H, m), 3.60(3H, m), 4.90(1H, m), 6.30(1H, m), 6.55(1H, m), 7.3-7.1(16H, m), 7.43(2H, m), 8.08(1H, m).

EXAMPLES 35–40

In a similar manner, the following compounds were prepared from the corresponding starting materials.

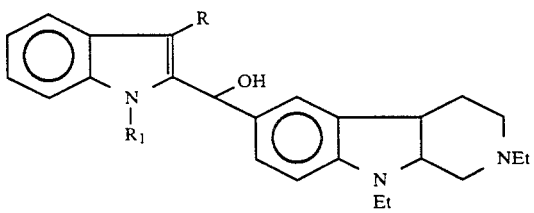

| Ex. No. | R | R$_1$ | Appearance | PMR (CDCl$_3$, δ) |
|---|---|---|---|---|
| 35 | —CH$_2$CH$_2$N(CH$_2$Ph)$_2$ | Me | Amorphous solid | 1.10(6H, m), 1.86(1H, m), 2.00(1H, m), 2.22(1H, m), 2.30-2.60 (5H, m), 2.69(2H, m), 2.91(1H, m), 2.95-3.25(3H, m), 3.35(1H, m), 3.45(3H, s), 3.63(5H, m), 6.03(1H, s), 6.35(1H, m), 6.86-7.01(2H, m), 7.10-7.35(14H, m), 7.56(1H, m) |
| 36 | —CH$_2$CH$_2$N(CH$_2$Ph)$_2$ | —CH$_2$Ph | Amorphous solid | 1.10(6H, m), 1.65(4H, m), 2.10(2H, m), 2.25-2.58(5H, m), 2.76 (2H, m), 2.92(3H, m), 3.05(1H, m), 3.30(1H, m), 3.50-3.71(5H, m), 5.45(2H, m), 6.25(1H, m), 6.75-7.10(5H, m), 7.15-7.35 (8H, m), 7.35(8H, m), 7.55(1H, m) |
| 37 | H | Me | Amorphous solid | 1.10(6H, m), 1.78(1H, m), 1.90(1H, m), 2.25(1H, m), 2.41(4H, m), 2.62(1H, m), 3.08(1H, m), 3.12(1H, m), 3.40(1H, m), 3.60 (3H, s), 3.70(1H, m), 5.94(1H, s), 6.40(2H, m), 7.07(3H, m), 7.19(1H, t, J=7.8Hz), 7.26(1H, m), 7.57(1H, d, J=7.8Hz) |
| 38 | —CH$_2$CH$_2$OCH$_2$Ph | Me | Amorphous solid | 1.10(6H, m), 1.3-1.5(2H, m), 1.72(3H, m), 1.90(1H, m), 2.25 (1H, m), 2.42(3H, m), 2.65(1H, m), 3.00-3.15(2H, m), 3.35(1H, m), 3.55(3H, s), 3.68(2H, m), 5.27(1H, dq, J=11.2, 1.5Hz), 5.71(1H, d, J=17.6Hz), 6.40(2H, m), 6.90-7.10(2H, m), 7.19 (1H, m), 7.26(7H, m), 7.94(1H, d, J=7.8Hz) |
| 39 | —CH$_2$CH$_2$OCH$_2$Ph | —CH$_2$Ph | Amorphous solid | 1.06(6H, m), 1.4-1.9(7H, m), 2.15(1H, m), 2.35(4H, m), 2.60 (1H, m), 2.90(1H, m), 3.05(1H, m), 3.30(1H, m), 3.58(1H, m), 5.1-5.8(4H, m), 6.30(2H, m), 6.65(1H, m), 6.80(2H, m), 6.9-7.2(8H, m), 7.32(3H, m), 7.70(1H, m) |
| 40 | —CH$_2$CH$_2$-(2-pyridyl) | —SO$_2$—C$_6$H$_4$—Me | Amorphous solid | 1.10(6H, m), 1.7-2.0(3H, m), 2.25(3H, s), 2.40(5H, m), 2.60 (1H, m), 3.05(5H, m), 3.30(2H, m), 6.28-6.45(2H, m), 6.60(1H, m), 6.85-7.10(5H, m), 7.20(1H, m), 7.28(1H, m), 7.45(4H, m), 8.10(1H, m), 8.39(1H, m) |

EXAMPLE 41

2,9-Diethyl-6-(1-(3-(2-methylethylamino)ethyl)-indole-2-yl)-ethyl)-1,2,3,4,4a,9a-hexahydro-pyrido[3,4-b]indole

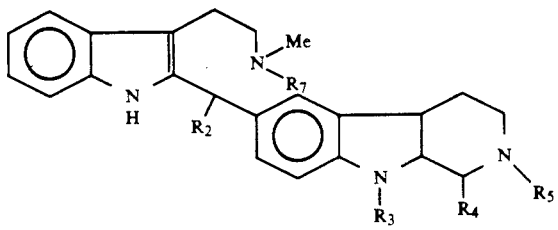

(I)

| Example No. | $R_2, R_7$ | $R_3$ | $R_4, R_5$ | Appearance | PMR (CDCl$_3$, δ) |
|---|---|---|---|---|---|
| 42 | —(CH$_2$)$_4$— | Me | H, Et | Amorphous solid | 1.13(3H, t, J=6.3Hz), 1.3–1.9(7H, m), 1.9–2.35(8H, m), 2.45(2H, q, J=6.3Hz), 2.5–2.8(4H, m), 2.8–3.1(5H, m), 3.19 (2H, m), 4.50(1H, m), 6.45(1H, t, J=8.6Hz), 6.85–7.25(5H, m), 7.53(2H, m) |
| 43 | —CH$_2$—〔C$_6$H$_4$〕—CH$_2$— | Et | H, Et | Amorphous solid | 1.15(6H, m), 1.85(4H, m), 2.25(2H, m), 2.45(4H, m), 2.55(1H, m), 2.81(2H, m), 2.9–3.5(6H, m), 3.6–4.0(4H, m), 4.95 (1H, m), 6.50(1H, m), 6.68(1H, m), 6.85–7.35(8H, m), 7.56 (2H, m) |
| 44 | —(CH$_2$)$_4$— | Me | —(CH$_2$)$_4$— | Amorphous solid | 1.3–2.3(19H, m), 2.5–3.2(11H, m), 3.42(3H, s), 4.50(1H, m), 6.50(1H, m), 6.80–7.25(5H, m), 7.53(1H, m), 7.65 (1H, m) |

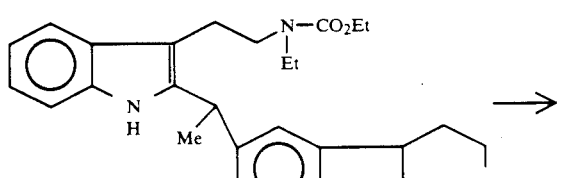

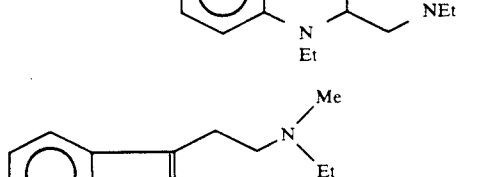

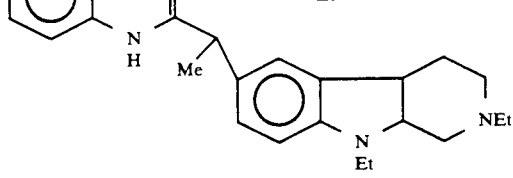

Lithium aluminium hydride (0.11 g) was added under ice-cooling to a solution of the compound prepared in Example 21 (0.76 g) in THF and the solution was heated at reflux for 5 hrs. Unreacted lithium aluminium hydride was decomposed with water and 15% aqueous NaOh solution. After filtration, the crude product was purified by column chromatography on silica gel. Eluates with 10% methanol/chloroform gave 0.40 g of the title compound.

Amorphous Solid

PMR (CDCl$_3$, δ) 1.10(9H, m), 1.64(3H, d, J=6.9 Hz), 1.85(2H, m), 2.1–2.8(13H, m), 2.98(3H, m), 3.11(1H, m), 3.35(1H, m), 3.62(1H, m), 4.49(1H, m), 6.40(1H, m), 6.90(2H, m), 7.07(2H, m), 7.20(1H, m), 7.5–7.7(2H, m).

EXAMPLES 42–44

In a similar manner, the following compounds were prepared from the corresponding starting materials.

EXAMPLE 45

6-(Benzyloxy-(3-(2-(N,N-dibenzylamino)ethyl)-1-methylindole-2-yl)-methyl)-2,9-diethyl-1,2,3,4,4a,9a-hexahydropyrido[3,4-b]indole

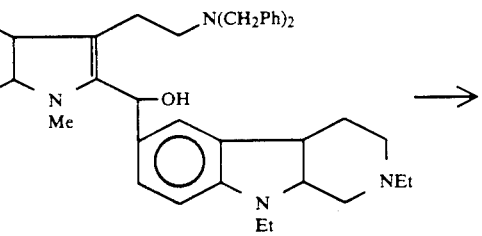

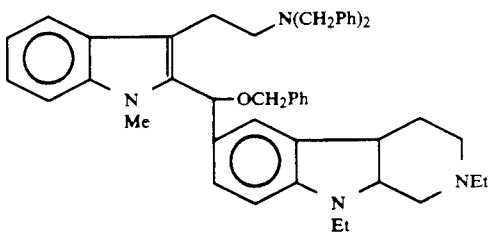

The compound prepared in Example 35 (0.25 g) and NaH (60% nujol, 0.03 g) were added under ice-cooling to anhydrous DMF solution, then benzyl bromide (0.05 ml) was added and the mixture was stirred at room temperature for 3 hrs. The reaction solution with the addition of water was extracted with ethyl acetate, washed with water and then brine and dried over magnesium sulfate. The crude product was purified by column chromatography on silica gel. Eluates with 3% methanol/chloroform gave 0.20 g of the title compound.

Amorphous Solid

PMR (CDCl$_3$, δ) 0.88(3H, t, J=6.8 Hz), 1.10(3H, t, J=7.4 Hz), 1.25(5H, m), 1.60(6H, m), 2.45(3H, m), 2.70(1H, m), 3.11(1H, m), 3.35(1H, m), 3.45(3H, s), 3.6-3.7(5H, m), 5.69(1H, s), 6.33(1H, m), 6.90(1H, m), 7.1-7.4(20H, m).

Further, the following illustrates the H$^+$/K$^+$ ATPase inhibitory activity assay and pharmaceutical preparations of the present compounds.

H$^+$/K$^+$ ATPase Inhibitory Activity Assay

The inhibitory activity was determined in the following manner using H$^+$/K$^+$ ATPase prepared from the stomach of pig.

H$^+$/K$^+$ ATPase dilute solution (100 μl, 50 μg as protein) was added to PIPES-tris (pH 6.2) buffer solution (440 μl) containing 4 mM magnesium chloride and 20 mM potassium chloride. Further, 0.1% ethanol solution of nigericin (5 μl) was added. To the solution was added dimethyl sulfoxide (5 μl) and the mixture was incubated at 37° C. for 30 minutes. Then 10 mM PIPES-tris buffer solution (450 μl) containing 4 mM ATP disodium was added to initiate the reaction. 30 minutes later, 50% trichloroacetic acid (1 μl) was added to cease the reaction. The amount of phosphorus released in this reaction was determined by a color development determination at 800 nm according to D. Lebel, G. Poirier et al. method (Anal. Biochem. 85, 86-89, 1978), at which the reading of the absorbance is taken as C1. On the other hand, a similar determination was carried out in the absence of potassium chloride, at which the reading of the absorbance is taken as C2. The inhibitory activity was determined by a similar procedure as in the above reaction, but adding 5 μl of a dimethyl sulfoxide solution containing 1 to 20 mg/ml of the inhibiting substance (test compound), instead of dimethyl sulfoxide. In that case, the readings of the absorbance in the presence and absence of potassium chloride are taken as T1 and T2, respectively.

% Inhibition (I) of the inhibiting substance (test compound) is calculated by the following equation.

$$I = [(C1 - C2) - (T1 - T2)] \times 100/(C1 - C2)$$

| Test Compound | H$^+$/K$^+$ ATPase % Inhibition |
|---|---|
| Example 1 | 54.9% (10 μg/ml) |
| Example 4 | 84% (20 μg/ml) |
| Exmaple 10 | 98.4% (5 μg/ml) |
| Example 11 | 97.5% (10 μg/ml) |
| Example 19 | 92.5% (10 μg/ml) |
| Example 34 | 80.8% (10 μg/ml) |
| Example 39 | 78.8% (10 μg/ml) |
| Example 40 | 24.4% (10 μg/ml) |
| Example 45 | 65.7% (10 μg/ml) |

The pharmaceutical preparations of the present compounds are shown below.

| Pharmaceutical Preparation 1 - Tablets (one tablet) | |
|---|---|
| Compound of Example 11 | 10 mg |
| Lactose | 67 mg |
| Crystalline cellulose | 15 mg |
| Corn starch | 7 mg |
| Magnesium stearate | 1 mg |

Each ingredient was uniformly blended to prepare powders for direct compression. The powders were formulated by a rotary tableting machine into tablets each 6 mm in diameter and weighing 100 mg.

| Pharmaceutical Preparation 2 - Granules (one divided form) | | |
|---|---|---|
| A. | Compound of Example 11 | 10 mg |
| | Lactose | 90 mg |
| | Corn starch | 50 mg |
| | Crystalline cellulose | 50 mg |
| B. | Hydroxypropylcellulose | 10 mg |
| | Ethanol | 9 mg |

The ingredients of A were uniformly blended and the solution of B was added. The mixture was kneaded and granulated by extrusion granulation. The granules were dried in a drier at 50° C. and then sieved into the grain size between 297 and 1460 μm. 200 mg of the granules were packed into a unit dosage form.

| Pharmaceutical Preparation 3 - Syrups | |
|---|---|
| Compound of Example 11 | 1.000 g |
| Refined sugar | 30.000 g |
| D-sorbitol 70 W/V % | 25.000 g |
| Ethyl p-hydroxybenzoate | 0.030 g |
| Propyl p-hydroxybenzoate | 0.015 g |
| Flavor | 0.200 g |
| Glycerol | 0.150 g |
| 96% Ethanol | 0.500 g |
| Distilled water | ad lib |

The compound, refined sugar, D-sorbitol, ethyl p-hydroxybenzoate and propyl p-hydroxybenzoate were dissolved in 60 ml of warmed water. After cooling, a solution of flavor dissolved in glycerol and ethanol was added. The whole mixture was diluted with water to balance 100 ml.

| Pharmaceutical Preparation 4 - Injections | |
|---|---|
| Compound of Example 11 | 1 mg |
| Sodium chloride | 10 mg |
| Distilled water | ad lib |

The compound and sodium chloride were dissolved in distilled water to balance 1.0 ml.

| Pharmaceutical Preparation 5 - Suppositories | |
|---|---|
| Compound of Example 11 | 2 g |
| Polyethylene glycol 4000 | 20 g |
| Glycerol | 78 g |

Polyethylene glycol 4000 was added to a solution of the compound in glycerol. The mixture was warmed and poured into a suppository mold and then cooled to give suppositories, each weighing 1.5 g.

What is claimed is:

1. A compound of formula (I)

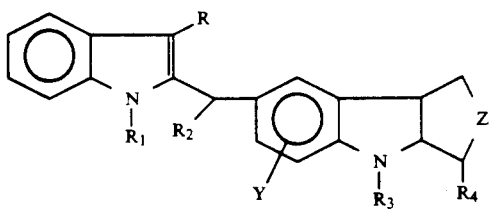 (I)

wherein
Y represents H, $C_1$-$C_6$ alkyl, $C_1$-$C_6$ alkoxy or halogen;
Z represents —$CH_2N(R_5)$—;
R represents H or —$CH_2CH_2X$ where X represents pyridyl, aralkyloxy or substituted amino of $NR_6R_7$ where $R_6$ represents H, $C_1$-$C_6$ alkyl, aralkyl, $C_1$-$C_6$ alkoxycarbonyl, aralkyloxycarbonyl or halogenated $C_1$-$C_6$ alkoxycarbonyl and $R_7$ represents H, $C_1$-$C_6$ alkyl or aralkyl, or together with $R_2$ may form a ring of —$(CH_2)_n$— (n is 1-4) or

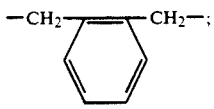

$R_1$ represents H, $C_1$-$C_6$ alkyl, aralkyl or arylsulfonyl;
$R_2$ represents $C_1$-$C_6$ alkyl, hydroxy, $C_1$-$C_6$ alkoxy or aralkyloxy;
$R_3$ represents H, $C_1$-$C_6$ alkyl, aralkyl or halogenated $C_1$-$C_6$ alkyl;
$R_4$ and $R_5$ may be the same or different and each represents H, $C_1$-$C_6$ alkyl or aralkyl or both may together form a ring of —$(CH_2)_m$— (m is 3 or 4);
or a pharmaceutically acceptable acid addition salt thereof.

2. A compound of claim 1 wherein R represents —$CH_2CH_2NR_6R_7$ where $R_6$ independently represents $C_1$-$C_4$ alkyl, benzyl, $C_1$-$C_4$ alkoxycarbonyl, benzyloxycarbonyl or halogenated $C_1$-$C_4$ alkoxy carbonyl and where $R_7$ independently represents $C_1$-$C_4$ alkyl or benzyl.

3. A compound of claim 1 wherein R represents H or —$CH_2CH_2NR_6R_7$ where $R_6$ represents $C_1$-$C_4$ alkyl, benzyl, $C_1$-$C_4$ alkoxycarbonyl, benzyloxycarbonyl or halogenated $C_1$-$C_4$ alkoxycarbonyl and $R_7$ together with $R_2$ forms a ring of —$(CH_2)_3$—, —$(CH_2)_4$— or

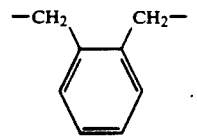

4. A compound of claim 1 wherein R represents —$CH_2CH_2X$ where X represents pyridyl or benzyloxy.

5. A compound of claim 1 wherein Z represents —$CH_2N(R_5)$— where $R_5$ represents $C_1$-$C_4$ alkyl or benzyl, or $R_5$ together with $R_4$ forms a ring of —$(CH_2)_4$—.

6. A compound of claim 1 wherein $R_1$ represents H, $C_1$-$C_4$ alkyl, benzyl or p-$C_1$-$C_4$ alkylphenylsulfonyl.

7. A compound of claim 1 wherein $R_2$ represents $C_1$-$C_4$ alkyl, hydroxy or benzyloxy.

8. A compound of claim 1 wherein Y represents H, $C_1$-$C_4$ alkyl, $C_1$-$C_4$ alkoxy or Cl.

9. A compound of claim 1 wherein $R_3$ represents $C_1$-$C_4$ alkyl, benzyl or halogenated $C_1$-$C_4$ alkyl.

10. A pharmaceutical composition which comprises as an active ingredient an effective amount of a compound of formula (I) as defined in claim 1 or a pharmaceutically acceptable acid addition salt thereof and a pharmaceutically acceptable carrier.

* * * * *